US006171344B1

(12) United States Patent
Atala

(10) Patent No.: US 6,171,344 B1
(45) Date of Patent: Jan. 9, 2001

(54) BLADDER SUBMUCOSA SEEDED WITH CELLS FOR TISSUE RECONSTRUCTION

(75) Inventor: Anthony Atala, Weston, MA (US)

(73) Assignee: Children's Medical Center Corporation, Boston, MA (US)

( * ) Notice: Under 35 U.S.C. 154(b), the term of this patent shall be extended for 0 days.

(21) Appl. No.: 08/912,127

(22) Filed: Aug. 15, 1997

Related U.S. Application Data

(60) Provisional application No. 60/024,069, filed on Aug. 16, 1996.

(51) Int. Cl.[7] .................................................... A61B 19/00
(52) U.S. Cl. ................................ 623/23.64; 623/23.66; 623/23.71; 623/23.72; 623/23.74; 623/23.76; 188/898
(58) Field of Search .................................. 623/11, 12, 66, 623/11.11, 23.64, 23.66, 23.71, 23.72, 23.74, 23.75, 23.76; 128/898

(56) References Cited

U.S. PATENT DOCUMENTS

| 4,172,128 | | 10/1979 | Thiele et al. ............................ 424/95 |
|---|---|---|---|
| 5,112,354 | | 5/1992 | Sires ........................................ 623/16 |
| 5,275,826 | | 1/1994 | Badylak et al. ....................... 424/551 |
| 5,352,463 | | 10/1994 | Badylak et al. ....................... 424/551 |
| 5,554,389 | * | 9/1996 | Badylak et al. ....................... 424/558 |
| 5,645,860 | * | 7/1997 | Knapp, Jr. et al. ................... 424/551 |
| 5,654,273 | | 8/1997 | Gallo et al. .............................. 514/12 |
| 5,711,969 | * | 1/1998 | Patel et al. ............................ 424/551 |
| 5,753,267 | * | 5/1998 | Badylak et al. ....................... 424/551 |
| 5,755,791 | * | 5/1998 | Whitson et al. ........................ 623/15 |
| 5,762,966 | * | 6/1998 | Knapp, Jr. et al. ................... 424/551 |

FOREIGN PATENT DOCUMENTS

| WO 9000395 | 1/1990 | (WO) . |
|---|---|---|
| WO 9305798 | 4/1993 | (WO) . |
| WO 9307913 | 4/1993 | (WO) . |
| WO 9631226 | 10/1996 | (WO) . |
| WO 9631232 | 10/1996 | (WO) . |

OTHER PUBLICATIONS

Ashkar, L. and Heller, E., "The Silastic Bladder Patch," *J. Urol.*, vol. 98, No. 6, 679–83 (1968).
Atala, A., "Commentary on the Replacement of Urologic Associated Mucosa," *J. Urol.*, vol. 156, 338–9 (1996).
Atala, A. et al., "Formation of Urothelial Structures in Vivo from Dissociated Cells Attached to Biodegradable Polymer Scaffolds in Vitro," *J. Urol.*, vol. 148, No. 2, pt. 2, 658–62 (1992).
Atala, A. et al., "Implantation in Vivo and Retrieval of Artificial Structures Consisting of Rabbit and Human Urothelium and Human Bladder Muscle," *J. Urol.*, vol. 150, No. 2, pt. 2, 608–12 (1993).
Cilento, B.G. et al., "Phenotypic and Cytogenetic Characterization of Human Bladder Urothelia Expanded in Vitro," *J. Urol.*, vol. 152, 665–70 (1994).

Hiles, M.C. et al., "Porosity of Porcine Small–Intestinal Submucosa for use as a Vascular Graft," *J. Biomed. Materials Research*, vol. 27, 139–44 (1993).
Kelâmi, A., "Lyophilized Human Dura as a Bladder Wall Substitute: Experimental and Clinical Results," *J. Urol.*, vol. 105, 518–22 (1971).
Kelâmi, A. et al., "Experimental Investigations of Bladder Regeneration Using Teflon–Felt as a Bladder Wall Substitute," *J. Urol.*, vol. 104, 693–8 (1970).
Kirker–Head, C.A., "Recombinant Bone Morphogenetic Proteins: Novel Substances for Enhancing Bone Healing," *Vet. Surg.*, vol. 24, No. 5, 408–19 (1995).
Kropp, B.P. et al., "Experimental Assessment of Small Intestinal Submucosa as a Bladder Wall Substitute," *Urology*, vol. 46, No. 3, 396–400 (1995).
Kudish, H.G., "The Use of Polyvinyl Sponge for Experimental Cystoplasty", *J. Urol.*, vol. 78, 232–235 (1957).
Laurencin, C.T. et al., "A Highly Porous 3–Dimensional Polyphosphazene Polymer Matrix for Skeletal Tissue Regeneration," *J. Biomed. Mater. Res.*, vol. 30, No. 2, 133–8 (1996).
Stein, J. et al., "Radical Cystectomy and Lower Urinary Tract Reconstruction After Cardiac Allograft Transplantation," *The Journal of Urology*, vol. 153, 415–6 (1995).
Sutherland, R.S. et al., "Regeneration of Bladder Urothelium, Smooth Muscle, Blood Vessels and Nerves into an Acellular Tissue Matrix," *J. Urol.*, vol. 156, 571–7 (1996).
Tobin, M.S. et al., "Maturational Response of Normal Human Urothelial Cells in Culture is Dependant on Extracellular Matrix and Serum Additives," *Surgical Forum*, vol. 45, 786–9 (1994).
Tsuji, I. et al., "Clinical Experiences of Bladder Reconstruction Using Preserved Bladder and Gelatin Sponge Bladder in the Case of Bladder Cancer," *J. Urol.*, vol. 98, 91–2 (1967).
Yaszemski, M.J. et al., "Evolution of Bone Transplantation: Molecular, Cellular and Tissue Strategies to Engineer Human Bone," *Biomaterials*, vol. 17, No. 2, 175–85 (1996).
Yoo, J.J. et al., "Ureteral Replacement using Biodegradable Polymer Scaffolds Seeded with Urothelial and Smooth Muscle Cells," *J. Urol.*, pt. 2, vol. 153, abst. No. 585, 375a (1995).
Zdrahala, R.J., "Small Caliber Vascular Grafts. Part I: State of the Art," *J. Biomater. Appl.*, vol. 10, No. 4, 309–29 (1996).
Probst, M. et al., "Reproduction of Functional Smooth Muscle Tissue and Partial Bladder Replacement," *British Journal of Urology*, vol. 79, 505–515 (1997).

* cited by examiner

*Primary Examiner*—Dinh X. Nguyen
(74) *Attorney, Agent, or Firm*—Lahive & Cockfield, LLP

(57) ABSTRACT

Methods and materials for tissue reconstruction, repair, and/or augmentation are disclosed. The invention provides isolated bladder submucosa seeded with cells for use in tissue reconstruction. The methods of the invention include the use of isolated bladder submucosa seeded with cells for augmentation of bladder and other organs and tissues.

12 Claims, 1 Drawing Sheet

BLADDER SUBMUCOSA SEEDED WITH CELLS FOR TISSUE RECONSTRUCTION

CROSS-REFERENCE TO RELATED APPLICATION

This application claims the benefit of priority under 35 U.S.C. 119(e) to co-pending U.S. provisional application Ser. No. 60/024,069, entitled "Biomaterials With Cells For Bladder Augmentation", filed Aug. 16, 1996, the entire content of which is hereby incorporated by reference.

BACKGROUND OF THE INVENTION

Reconstructive surgery has been used for many years for the treatment of congenital tissue defects and for repair of damaged organs and tissues. An ideal material for tissue reconstruction should be biocompatible, able to incorporate into the native tissue without inducing an adverse tissue response, and should have adequate anatomical and functional properties (for example, size, strength, durability, and the like). Although a large number of bio-materials, including synthetic and naturally-derived polymers, have been employed for tissue reconstruction or augmentation (see, e.g., "Textbook of Tissue Engineering" Eds. Lanza, R., Langer, R., and Chick, W., ACM Press, Colorado (1996) and references cited therein), no material has proven satisfactory for use in every application.

For example, in the field of bladder reconstruction, synthetic biomaterials such as polyvinyl and gelatin sponges, polytetrafluoroethylene (Teflon) felt, and silastic patches have been relatively unsuccessful, generally due to foreign body reactions (see, e.g., Kudish, H. G., *J. Urol.* 78:232 (1957); Ashkar, L. and Heller, E., *J. Urol.* 98:91 (1967); Kelami, A. et al., *J. Urol.* 104:693 (1970)). Polymeric materials have been used as "scaffolds" for seeding cells; the seeded scaffolds can be implanted to provide a matrix for the growth of new tissue (see, e.g., Atala, A. et al., *J. Urol.* 148 (2 Pt 2): 658–62 (1992); Atala, A., et al. *J. Urol.* 150 (2 Pt 2): 608–12 (1993)). Naturally-derived materials such as lyophilized dura, de-epithelialized bowel segments, and small intestinal submucosa (SIS) have also been proposed for bladder replacement (for a general review, see Mooney, D. et al., "Tissue Engineering: Urogenital System" in "Textbook of Tissue Engineering" Eds. Lanza, R., Langer, R., and Chick, W., ACM Press, Colorado (1996)).

It has been reported that bladders augmented with dura, peritoneum, placenta and fascia contract over time (Kelami, A. et al., *J. Urol.* 105:518 (1971)). De-epithelized bowel segments demonstrated an adequate urothelial covering for use in bladder reconstruction, but difficulties remain with either mucosal regrowth, segment fibrosis, or both. It has been shown that de-epithelization of the intestinal segments may lead to mucosal regrowth, whereas removal of the mucosa and submucosa may lead to retraction of the intestinal segment (see, e.g., Atala, A., *J. Urol.* 156:338 (1996)).

Xenogenous porcine SIS has been used recently with favorable results (e.g., Kropp, B. P. et al, *Urology* 46:396 (1995)). This biodegradable collagen-rich xenogenic membrane had been previously studied as a potential material for vascular grafts (see, e.g., Hiles et al., *J. Biomed. Materials Research* 27:139 (1993)). However, SIS may be limited by the maximum size the graft can cover, which may not be sufficient for bladder replacement.

Other problems have been reported with the use of certain gastrointestinal segments for bladder surgery, including infection, perforation, stone formation, metabolic derangements and instances of tumor development. Formalin-preserved sections of bladder have been used for bladder reconstruction (see, e.g., Tsuji et al., *J. Urol.* 98:91 (1967)). However, the use of the formalin-preserved material generally did not result in effective long-term treatment.

Polymeric and naturally-derived "scaffolds" have also been used to support the regrowth of bone into bone defects (see, e.g., U.S. Pat. Nos. 5,112,354 and 4,172,128; for a general review, see Yaszemski, M. J.; et al., *Biomaterials* 17 (2): 175–85 (1996) and references cited therein). Bone-derived collagen implants have been used for bone repair. However, these materials do not always provide the requisite strength, flexibility, or non-immunogenicity needed for long-term repair of bone.

SUMMARY OF THE INVENTION

The present invention relates to materials and methods for repairing or augmenting tissues. More particularly, the invention relates to methods for tissue reconstruction or repair using bladder submucosa, to methods for preparing bladder submucosa segments suitable for use in tissue reconstruction or repair, and to materials for use in tissue reconstruction or repair. The invention also relates to the use of isolated bladder submucosa seeded with cells for repair, reconstruction, or augmentation of tissues or organs.

In one aspect, the invention provides a method for augmenting a tissue of a subject. The method includes the step of augmenting the tissue of the subject with isolated bladder submucosa seeded with cells. In preferred embodiments, the isolated bladder submucosa is seeded with cells of a type found in the tissue of the subject. The tissue of the subject can be bladder tissue. The isolated bladder submucosa can be allogenic bladder submucosa or xenogeic bladder submucosa. The isolated bladder submucosa seeded with cells can further include a growth factor for promoting growth of the tissue. The subject can be a mammal, including a human.

In another embodiment, the invention provides a method for repairing a damaged tissue, the method comprising contacting the damaged tissue with isolated bladder submucosa seeded with cells, under conditions such that growth of the tissue occurs, such that the damaged tissue is repaired. In certain embodiments, the damaged tissue is bladder tissue.

In another embodiment, the invention provides a method for increasing bladder capacity of a subject having a bladder. The method includes surgically grafting isolated bladder submucosa to the bladder of the subject, such that the bladder capacity is increased.

In another aspect, the invention provides a material for reconstruction, repair or augmentation of a subject's tissue. The material comprises isolated bladder submucosa seeded with cells. In certain embodiments, the isolated bladder submucosa is obtained from whole bladder tissue by microdissection; the isolated bladder submucosa can optionally be further treated to ensure an acellular material is obtained. In certain preferred embodiments, the isolated bladder submucosa has first and second surfaces and is seeded with urothelial cells on the first surface and is seeded with muscle cells on the second surface; this material is especially useful for bladder reconstruction, augmentation, and repair.

In another aspect, the invention provides a method for preparing a material which comprises isolated bladder submucosa seeded with cells. The method comprises obtaining isolated bladder submucosa and seeding the isolated bladder submucosa with cells. In preferred embodiments, the isolated bladder submucosa is obtained from whole bladder tissue by microdissection; the isolated bladder submucosa can optionally be further treated to ensure an acellular material is obtained. In certain preferred embodiments, the isolated bladder submucosa has first and second surfaces and the step of seeding the isolated bladder submucosa with cells comprises seeding the isolated bladder submucosa with urothelial cells on the first surface and with muscle cells on the second surface. The method can optionally include the further step of adding a growth factor to the isolated bladder submucosa.

DETAILED DESCRIPTION OF THE INVENTION

Figure 1:
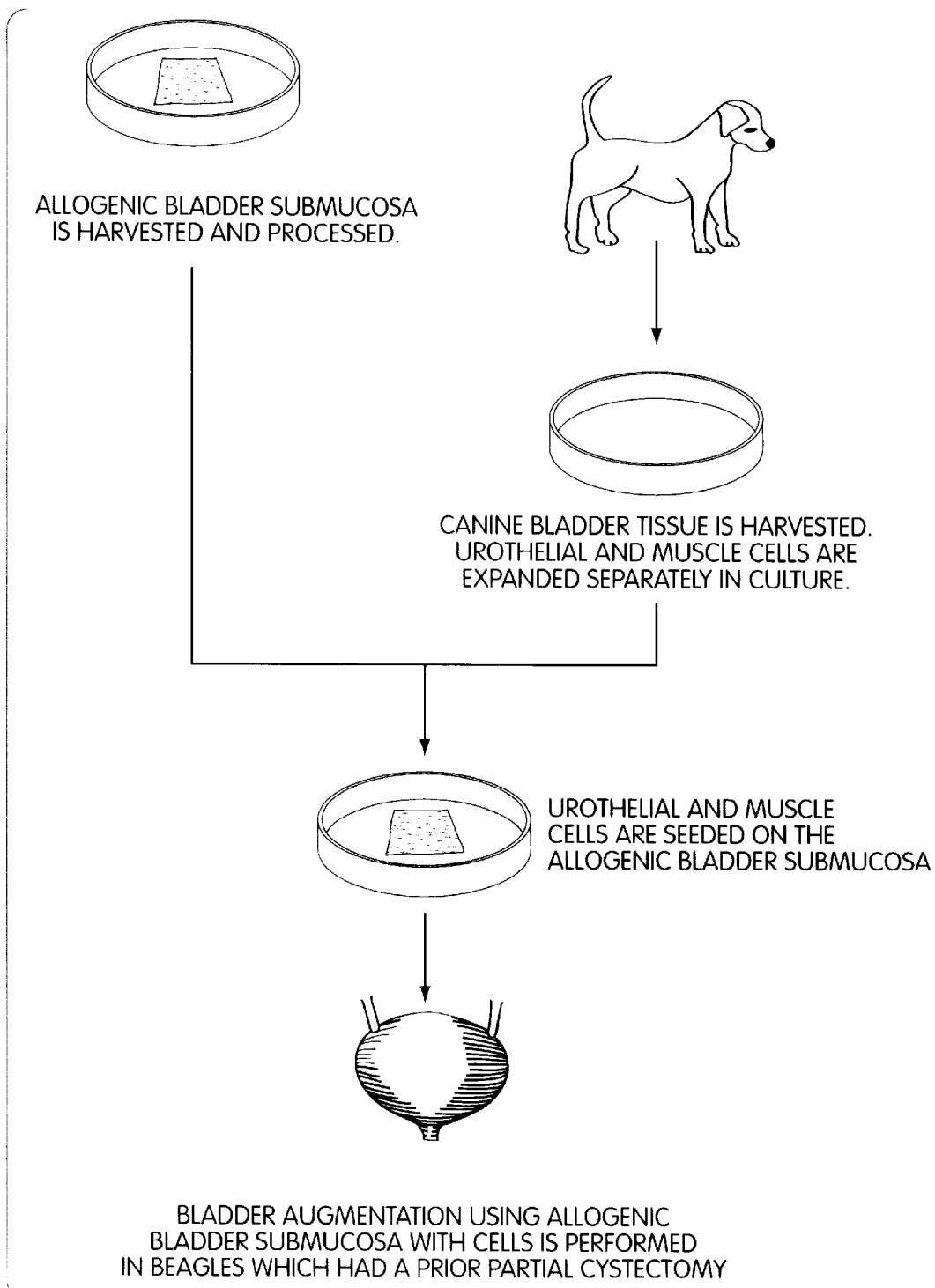
FIG. 1 is a schematic diagram showing harvesting of bladder submucosa and cells, and bladder augmentation with the isolated bladder submucosa seeded with cells.

The present invention provides methods and materials for tissue reconstruction and repair. In general, the invention features the use of isolated bladder submucosa for tissue repair and augmentation.

Biodegradable polymers have been used as cell delivery vehicles for bladder repair wherein reconstituted muscle cells were layered on one side of the polymer and urothelial cells were layered on the opposite side. The in vitro cell-polymer construct was then used for tissue replacement in animal bladders, ureters and urethras (see, e.g., Atala, A. et al., *J. Urol.* 148 (2 Pt 2): 658–62 (1992); Atala, A., et al. *J. Urol.* 150 (2 Pt 2):608–12 (1993); Yoo, J. J. et al., *J. Urol.* Pt. 2, 153:375A (1995)). Although the polymers were adequate for certain purposes, isolated bladder submucosa has specific characteristics, such as elasticity, which are desirable for use in tissue repair, reconstruction, and augmentation.

Bladder tissue in vivo contains three principal layers: the submucosal layer, the muscle layer, and the urothelial layer. As used herein, the term "isolated bladder submucosa" refers to bladder submucosa which is substantially free of naturally-occurring urothelial and muscle layers of bladder. In preferred embodiments, isolated bladder submucosa is substantially free of naturally-occurring adherent muscle and urothelial cells (i.e., isolated bladder submucosa is preferably substantially free of muscle and urothelial cells which were part of the naturally-occurring bladder tissue from which the isolated bladder submucosa was obtained, and which cells were not removed from the submucosa, e.g., by microdissection). Isolated bladder submucosa is a collagen-rich layer which is substantially non-immunogenic, acellular, and bioresorbable. Commonly-owned copending U.S. patent application entitled "Isolated Bladder Submucosa For Tissue Reconstruction", filed on even date herewith, hereby incorporated by reference, describes the use of isolated bladder submucosa, without added cells, for tissue repair and reconstruction.

"Isolated bladder submucosa seeded with cells" refers to isolated bladder submucosa from which substantially all naturally-occurring adherent cells have been removed (as described herein), and to which exogenous cells have been added. The term "exogenous" cells, as used herein, refers to cells which are added in vitro to isolated bladder submucosa. Thus, for example, exogenous cells include cells obtained from cell culture or from separate tissue samples. Exogenous cells can be obtained from a sample of whole bladder tissue from which isolated bladder submucosa is obtained; however, such cells must be first separated from the submucosa before the isolated submucosa is seeded with the cells. For example, as described in the Example, infra, microdissection of whole bladder tissue can separate the submucosa layer from the urothelial layer and the muscular layer. Cells obtained from the muscle or urothelial tissue can then be cultured in vitro, and the cultured cells seeded onto isolated submucosa. Exogenous cells also include cells obtained from organs or tissues other than bladder, such as endothelial cells (e.g., from vascular tissue), osteoblasts from bone, and the like.

Isolated bladder submucosa can be obtained, e.g., according to the methods described herein. For example, sections of bladder harvested from a subject can be microdissected to remove the muscle and urothelial layers from the submucosa (e.g., as described in the Example, infra) to produce isolated bladder submucosa, which, in certain embodiments, can be washed, e.g., with phosphate-buffered saline (PBS) to remove extraneous materials, blood, and the like. In certain embodiments, isolated bladder submucosa (e.g., prepared by microdissection) can be further treated to ensure that the isolated bladder submucosa preparation is acellular. For example, sections of microdissected bladder submucosa can be placed in distilled water to lyse any remaining cells which adhere to the collagenous submucosal layer. Further treatments, e.g., with a deoxyribonuclease to remove any remaining nucleic acids, can be employed to further ensure that isolated bladder submucosa is cell-free (prior to seeding with exogenous cells). Such treatments will be routine to one of ordinary skill in the art in light of the teachings herein (see also Sutherland, R. S., et al. *J. Urol.* 156:571 (1996)).

Cells for seeding onto isolated bladder submucosa can be obtained by standard methods and will in general be selected to be compatible with the target tissue or organ which is being repaired or augmented. The seeded cells are preferably of a type which can normally be found in the target organ or tissue. In preferred embodiments, the cells are cells obtained from a donor animal of the same species as the subject (e.g., as shown in FIG. 1), to avoid or reduce immunogenic responses in the host after implantation. Such cells are referred to herein as "allogenic" cells. In certain preferred embodiments, the seeded cells can be obtained from the subject (autologous cells) prior to surgery. Cells (such as autologous cells) can be cultured in vitro, if desired, to increase the number of cells available for seeding on the isolated bladder submucosa "scaffold". The use of allogenic cells, and more preferably autologous cells, is preferred to prevent tissue rejection. However, if an immunological response does occur in the subject after implantation of the isolated bladder submucosa seeded with cells (which could lead to graft rejection), the subject can be treated, e.g., with immunosuppresive agents such as cyclosporin or FK506, to reduce the likelihood of rejection of the implanted material. In certain embodiments, chimeric cells, or cells from a transgenic animal, can be seeded onto the isolated bladder submucosa.

Seeding of cells onto the isolated bladder submucosa can be performed, e.g., as described in the Example or according to standard methods. For example, the seeding of cells onto polymeric substrates for use in tissue repair has been reported (see, e.g., Atala, A. et al., *J. Urol.* 148 (2 Pt 2): 658–62 (1992); Atala, A., et al. *J. Urol.* 150 (2 Pt 2): 608–12 (1993)). In certain preferred embodiments, more than one cell type can be seeded onto isolated bladder submucosa prior to implantation. Illustratively, as described in the Example, infra, isolated bladder submucosa can be seeded on one side or surface with urothelial cells, and on a second side or surface with muscle cells, prior to implantation of the graft. In certain embodiments, more than one cell type can be seeded onto a single surface of the isolated bladder submucosa. Cells grown in culture can be trypsinized to separate the cells, and the separated cells can be seeded on the isolated bladder submucosa. Alternatively, cells obtained from cell culture can be lifted from a culture plate as a cell layer, and the cell layer can be directly seeded onto the isolated bladder submucosa without prior separation of the cells. In a preferred embodiment, at least 50 million cells/cm$^2$ are seeded onto a surface of isolated bladder submucosa. However, it will be appreciated that the density of cells seeded onto the bladder submucosa can be varied. For example, greater cells densities promote greater tissue formation by the seeded cells, while lesser densities may permit relatively greater formation of tissue by cells infiltrating the graft from the host. Selection of cell types, and seeding of cells onto isolated bladder submucosa, will be routine to one of ordinary skill in the art in light of the teachings herein.

Isolated bladder submucosa can be treated with additives or drugs prior to implantation (before or after the isolated bladder submucosa is seeded with cells), e.g., to promote the formation of new tissue after implantation. Thus, for example, growth factors, cytokines, extracellular matrix components, and other bioactive materials can be added to the isolated bladder submucosa to promote graft healing and formation of new tissue. Such additives will in general be selected according to the tissue or organ being reconstructed or augmented, to ensure that appropriate new tissue is formed in the engrafted organ or tissue (for examples of such additives for use in promoting bone healing, see, e.g., Kirker-Head, C. A. *Vet. Surg.* 24 (5): 408–19 (1995)). For example, when isolated bladder submucosa seeded with endothelial cells is used to augment vascular tissue, vascular endothelial growth factor (VGEF, see, e.g., U.S. Pat. No. 5,654,273) can be employed to promote the formation of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the isolated bladder submucosa. Such additives are preferably provided in an amount sufficient to promote the formation of new tissue of a type appropriate to the tissue or organ which is to be repaired or augmented (e.g., by causing or accelerating infiltration of host cells into the graft).

While reference is made herein to augmentation of bladder according to the invention, it will be understood that the methods and materials of the invention are useful for tissue reconstruction or augmentation of a variety of tissues and organs in a subject. Thus, for example, organs or tissues such as bladder, ureter, urethra, renal pelvis, and the like, can be augmented or repaired with isolated bladder submucosa seeded with cells. The materials and methods of the invention further can be applied to the reconstruction or augmentation of vascular tissue (see, e.g., Zdrahala, R. J., *J. Biomater. Appl.* 10 (4): 309–29 (1996)), intestinal tissues, stomach, cartilage, bone (see, e.g., Laurencin, C. T. et al., *J. Biomed. Mater. Res.* 30 (2): 133–8 1996), and the like. The term "subject," as used herein, refers to a mammal, such as a dog, cat, pig, horse, cow, or human, in need of reconstruction, repair, or augmentation of a tissue.

Isolated bladder submucosa can be obtained from whole bladder tissue as described herein. Acellular isolated bladder submucosa is believed to be substantially non-immunogenic. In certain preferred embodiments, isolated bladder submucosa for tissue repair or augmentation is obtained from an animal of the same species as the subject; such tissue is referred to herein as "allogenic" bladder submucosa. However, the substantially non-immunogenic qualities of isolated bladder submucosa can permit the use of isolated bladder submucosa obtained from a species different from the subject (referred to herein as "xenogenic" isolated bladder submucosa). The use of xenogenic isolated bladder submucosa is especially advantageous when allogenic isolated bladder submucosa is difficult to obtain, e.g., when the subject is a human. Thus, isolated bladder submucosa can be obtained from animals, such as pigs, from which adequate quantities are readily available, for use in repair or augmentation of tissues or organs of a subject of another species. As previously mentioned, however, allogenic cells are preferred for seeding on the isolated bladder submucosa. Additionally, isolated bladder submucosa can be obtained from cadavers.

In a preferred embodiment, the materials and methods of the invention are useful for the reconstruction or augmentation of bladder tissue. Thus, the invention provides treatments for such conditions as bladder exstrophy, bladder volume insufficiency, reconstruction of bladder following partial or total cystectomy, repair of bladder damaged by trauma, and the like.

It has now been found that isolated bladder submucosa can permit the formation of new tissue having a grossly normal cellular organization. For example, as described in the Example, infra, isolated bladder submucosa seeded with urothelial and muscle cells and grafted into bladder served as a "scaffold" for the formation of new bladder tissue within about two months. The new tissue consisted of a urothelial-lined lumen surrounded by submucosal tissue and smooth muscle. Moreover, the newly-formed tissue showed evidence of angiogenesis, and nerve growth. Without wishing to be bound by any theory, it is believed that cells from the host animal can infiltrate and grow on the isolated bladder submucosa graft, thereby providing new tissue which is structurally and functionally similar to native tissue, e.g., bladder tissue. The seeded cells may also grow to form new tissue. It is believed that isolated bladder submucosa seeded with cells is generally not resorbed after implantation. However, in certain instances, the isolated bladder submucosa may be resorbed as new tissue is formed.

Grafting of isolated bladder submucosa seeded with cells to an organ or tissue to be augmented can be performed according to the methods described herein or according to art-recognized methods. Thus, for example, isolated bladder submucosa seeded with cells can. be grafted to an organ or tissue of the subject by suturing the graft material to the target organ, e.g., as described in Example 1, infra. Other methods for attaching a graft to an organ or tissue of the subject (e.g., by use of surgical staples) may also be employed. Such surgical procedures can be performed by one of ordinary skill in the art according to known procedures.

The methods and materials of the invention have been found to be useful in bladder augmentation, as described herein. In a preferred embodiment, isolated bladder submucosa seeded with cells is used for augmentation of bladder, to provide an augmented bladder having a volume (capacity) at least about 20% greater than the pre-augmentation capacity, more preferably at least about 40% greater, 60% greater, 80%, 100%, 200% or 300% greater bladder capacity. In general, it is believed that grafts of isolated bladder submucosa seeded with cells do not significantly contract over time after implantation. Without wishing to be bound by theory, it is believed that the seeded cells can inhibit or prevent self-adherence and contraction of the grafted material. However, if desired, the graft site (or the isolated bladder submucosa seeded with cells) can be treated with materials for preventing self-adherence of the graft material, thereby preventing contraction of the grafted bladder and providing increased bladder capacity in the subject. Materials for the prevention of surgical adhesions are commercially available.

EXAMPLE

Ten beagles were anesthetized with sodium pentobarbital (25 mg/kg IV) following pretreatment with acepromazine (0.2 mg/kg IM). Beagles underwent partial cystectomies, removing approximately 50% of their bladders. In five, the bladder tissue was microdissected and the mucosal and muscular layers separated. The bladder urothelial and muscle cells were cultured using a previously-described technique (see, e.g., Cilento, B. G. et al., *J. Urol.* 152:665 (1994); Tobin, M. S. et al., *Surgical Forum* 45:786 (1994); Freeman, M. R. et al. *J. Urol.* 153:4 (suppl.) (1995)). Briefly, urothelial cells were dissected and placed in serum and free keratinocyte growth medium (Keratinocyte SFM, Gibco, Grand Island, N.Y.) containing 5 ng/mL epidermal growth factor and 50 ug/mL bovine pituitary extract. Muscle cells were processed by the tissue explant technique using Dulbecco's Modified Eagle's Medium (DMEM) (HyClone Laboratories, Inc., Logan, Utah) supplemented with 10% fetal calf serum. The cells were incubated in a humidified atmosphere chamber containing 5% $CO_2$ and maintained at 37° C.

Canine bladder tissue was aseptically obtained from sacrificed animals. The bladder tissue was repeatedly rinsed with phosphate buffered saline (PBS). The submucosa was microdissected and isolated from the muscular and serosal layers. The isolated submucosa was thoroughly washed and placed in PBS containing 10% cefazolin. The submucosa was then kept at 4° C. for 6 to 12 months. All segments of allogenic bladder submucosa, measuring 4×5 cm in size, were exposed to UV light for 24 hours to sterilize the segments. Five segments were seeded with the in vitro expanded muscle cells on one side and urothelial cells on the opposite side. These cell-submucosa scaffolds were left in culture for 7 days before implantation.

Preoperative fluoroscopic cystography and urodynamic studies were performed in all animals. Under general anesthesia, five beagles underwent cruciate cystotomies on the bladder dome. Augmentation cystoplasty was performed with the allogenic bladder submucosa seeded with urothelial and muscle cells. A single layer of continuous interlocking sutures with 4-0 vicryl was used for anastomosis. 5-0 Nylon nonabsorbable sutures were placed at the four surgical corners as markers. The augmented bladders were covered with omentum. Cystostomy catheters were used for urinary diversion for 10 to 14 days. Urodynamic studies and fluoroscopic cystography were performed in all dogs at one, two and three months post-operatively. The augmented bladders were retrieved two and three months after augmentation and examined grossly and histologically with hematoxylin and eosin stains.

Results

During the duration of the study, none of the dogs demonstrated any untoward effects. All animals survived until the time of sacrifice without any noticeable complications such as urinary tract infection or calculi formation. Fluoroscopic cystography of all the augmented bladders showed a normal bladder configuration without any leakage at one, two and three months after the procedure.

Bladders augmented with the allogenic bladder submucosa seeded with cells showed an average increase in capacity of 99%. All animals showed a normal bladder compliance as evidenced by the urodynamic studies.

At retrieval, the augmented bladders appeared grossly normal without any evidence of diverticular formation in the region of the graft. The thickness of the grafted segment was similar to that of the native bladder tissue. There was no evidence of adhesion or fibrosis. Histologically, all retrieved bladders contained a normal cellular organization consisting of a urothelial lined lumen surrounded by submucosal tissue and smooth muscle. An angiogenic response was evident in all specimens.

The results show that bladder submucosa seeded with urothelial and muscle cells is able to form a new bladder tissue which can be histologically and functionally indistinguishable from the native bladder. Without wishing to be bound by theory, this result may be due to a possible maintenance of the architectural frame of the bladder by the extracellular matrix regenerated by the seeded cells. The urothelial and muscle cells seeded on the allogenic submucosa appear to prevent the resorption of the graft. These results suggest that bladder submucosa, a material consisting of non-immunogenic acellular natural collagen, seeded with cells, is a suitable biomaterial for tissue repair and reconstruction, e.g., for bladder augmentation. This technology is able to form new bladder tissue which appears anatomically and functionally similar to that of normal bladders.

Those skilled in the art will recognize, or be able to ascertain using no more than routine experimentation, numerous equivalents to the specific procedures described herein. Such equivalents are considered to be within the scope of this invention and are covered by the following claims. The contents of all publications and patent applications cited herein are hereby incorporated by reference. Other embodiments are within the following claims.

What is claimed is:

1. A method for surgically augmenting a tissue of a subject, the method comprising augmenting the tissue of the subject with isolated bladder submucosa seeded with cells, wherein said submucosa is obtained by microdissection of bladder tissue.

2. The method of claim 1, wherein the isolated bladder submucosa is seeded with cells of a type found in the tissue of the subject.

3. The method of claim 1, wherein the tissue of the subject is bladder tissue.

4. The method of claim 1, wherein the isolated bladder submucosa is allogenic bladder submucosa.

5. The method of claim 1, wherein the subject is a human.

6. The method of claim 1, wherein the isolated bladder submucosa is xenogenic bladder submucosa.

7. The method of claim 1, wherein the isolated bladder submucosa seeded with cells further comprises a growth factor for promoting growth of the tissue.

8. A method for repairing a damaged tissue, the method comprising contacting the damaged tissue with isolated bladder submucosa seeded with cells, under conditions such that growth of the tissue occurs, such that the damaged tissue is repaired, wherein said submucosa is obtained by microdissection of bladder tissue.

9. The method of claim 8, wherein the damaged tissue is bladder tissue.

10. A material for tissue reconstruction or augmentation, the material comprising isolated bladder submucosa seeded with cells, wherein said submucosa is obtained by microdissection of bladder tissue.

11. The material of claim 10, wherein the isolated bladder submucosa has first and second surfaces and is seeded with urothelial cells on the first surface and is seeded with muscle cells on the second surface.

12. A method for preparing isolated bladder submucosa seeded with cells, the method comprising the steps of:
    obtaining isolated bladder submucosa by microdissection of bladder tissue; and
    seeding the isolated bladder submucosa with cells.

* * * * *